(12) United States Patent
Shindo et al.

(10) Patent No.: US 8,868,370 B2
(45) Date of Patent: Oct. 21, 2014

(54) SAMPLE ANALYZING SYSTEM, SAMPLE ANALYZER AND MANAGEMENT APPARATUS

(75) Inventors: Naoki Shindo, Akashi (JP); Yusuke Suga, Kobe (JP); Aya Konishi, Nishinomiya (JP); Daigo Fukuma, Kobe (JP); Keisuke Kuwano, Kobe (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 330 days.

(21) Appl. No.: 13/240,536

(22) Filed: Sep. 22, 2011

(65) Prior Publication Data
US 2012/0078514 A1 Mar. 29, 2012

(30) Foreign Application Priority Data
Sep. 24, 2010 (JP) .................................. 2010-214540

(51) Int. Cl.
G06F 19/00 (2011.01)
G01N 35/00 (2006.01)

(52) U.S. Cl.
CPC ........ *G01N 35/00871* (2013.01); *G06F 19/366* (2013.01); *G06F 19/3412* (2013.01)
USPC ............... 702/119; 702/21; 702/62; 702/189; 707/602; 717/157

(58) Field of Classification Search
CPC ................ G01N 35/0054; G01N 2035/00881; G01N 2035/00891; G01N 35/00871; G06F 19/3412; G06F 19/366
USPC ............ 702/68, 80, 119, 120, 122, 123, 183, 702/189, 21, 62; 707/602; 717/133, 157
See application file for complete search history.

(56) References Cited

U.S. PATENT DOCUMENTS

| 6,604,110 B1 * | 8/2003 | Savage et al. ................. 707/602 |
| 7,739,079 B2 * | 6/2010 | Naito ............................ 702/189 |
| 2006/0218543 A1 * | 9/2006 | Boger ........................... 717/157 |

FOREIGN PATENT DOCUMENTS

JP 2009-085885 A 4/2009

* cited by examiner

*Primary Examiner* — John H Le
(74) *Attorney, Agent, or Firm* — Brinks Gilson & Lione

(57) ABSTRACT

The present invention is a sample analyzing system, including a sample analyzer and a management apparatus connected to the sample analyzer via a communication network. The management apparatus includes: a first memory that stores a computer program for the sample analyzer and manual data which corresponds to a version of the computer program; a first communication device; and a first controller configured to transmit, via the first communication device to the sample analyzer, the computer program and the manual data corresponding to the version of the computer program stored in the first memory. The sample analyzer includes: a second communication device; a second memory that stores the computer program and the manual data received by the second communication device; and a second controller configured to execute the computer program stored in the second memory.

18 Claims, 12 Drawing Sheets

FIG.5

FILE INFORMATION OF MANAGEMENT APPARATUS

| PS CODE TYPE | VERSION | REGION | PROGRAM | LANGUAGE | MANUAL |
|---|---|---|---|---|---|
| PS CODE A TYPE | Ver.01 | JAPAN | Ver.01 | JAPANESE | Ver.01 |
| | | AMERICA | Ver.01 | ENGLISH | Ver.01 |
| | | ... | ... | ... | ... |
| | Ver.02 | JAPAN | Ver.02 | JAPANESE | Ver.02 |
| | | AMERICA | Ver.02 | ENGLISH | Ver.02 |
| | | ... | ... | ... | ... |
| | Ver.03 | JAPAN | Ver.03 | JAPANESE | Ver.03 |
| | | AMERICA | Ver.03 | ENGLISH | Ver.03 |
| | | ... | ... | ... | ... |
| ... | ... | ... | ... | ... | ... |

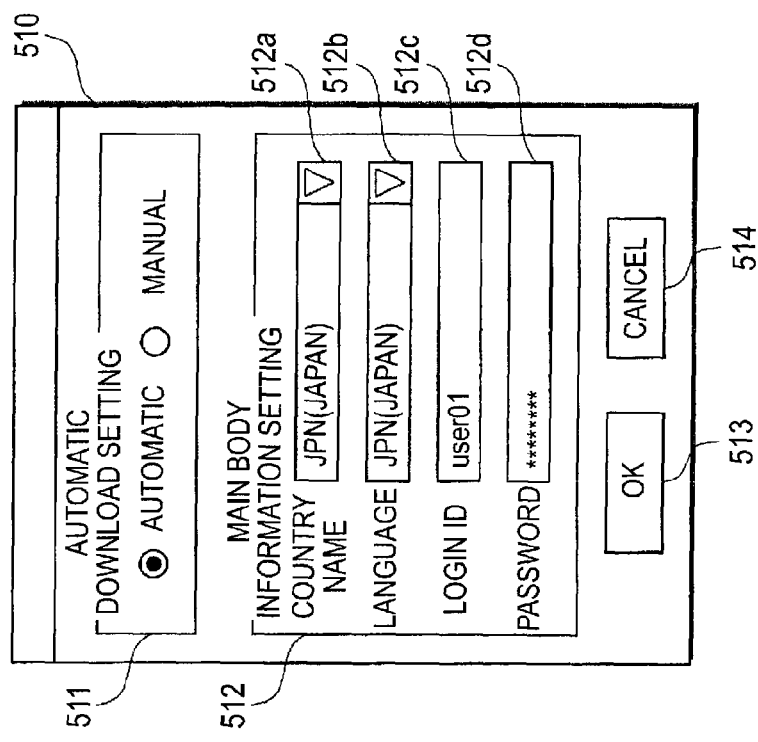

FIG.7A

ANALYZER INFORMATION OF INFORMATION PROCESSOR

| ANALYZER | PS CODE | SERIAL NUMBER | DEVICE NAME | EXECUTION VERSION | | | HOLDING VERSION | | |
|---|---|---|---|---|---|---|---|---|---|
| | | | | PROGRAM VERSION | PROGRAM | MANUAL | PROGRAM VERSION | PROGRAM | MANUAL |
| FIRST ANALYZER | A0000001 | 00012 | analyzerA1 | Ver.02 | Ver.02 | Ver.02 | | | |
| SECOND ANALYZER | A0000001 | 00013 | analyzerA2 | Ver.02 | Ver.02 | Ver.02 | | | |
| THIRD ANALYZER | B0000004 | 00040 | analyzerB4 | Ver.02 | Ver.02 | Ver.02 | | | |

FIG.7B

ANALYZER INFORMATION OF INFORMATION PROCESSOR AFTER DOWNLOAD

| ANALYZER | PS CODE | SERIAL NUMBER | DEVICE NAME | EXECUTION VERSION | | | HOLDING VERSION | | |
|---|---|---|---|---|---|---|---|---|---|
| | | | | PROGRAM VERSION | PROGRAM | MANUAL | PROGRAM VERSION | PROGRAM | MANUAL |
| FIRST ANALYZER | A0000001 | 00012 | analyzerA1 | Ver.02 | Ver.02 | Ver.02 | Ver.03 | Ver.03 | Ver.03 |
| SECOND ANALYZER | A0000001 | 00013 | analyzerA2 | Ver.02 | Ver.02 | Ver.02 | Ver.03 | Ver.03 | Ver.03 |
| THIRD ANALYZER | B0000004 | 00040 | analyzerB4 | Ver.02 | Ver.02 | Ver.02 | | | |

STORAGE INFORMATION OF INFORMATION PROCESSOR

| PS CODE | SERIAL NUMBER | DEVICE NAME | PROGRAM VERSION | STORAGE VERSION | |
|---|---|---|---|---|---|
| | | | | PROGRAM | MANUAL |
| A0000001 | 00012 | analyzerA1 | Ver.01 | Ver.01 | Ver.01 |
| A0000001 | 00013 | analyzerA2 | Ver.02 | Ver.02 | Ver.02 |
| | | | Ver.01 | Ver.01 | Ver.01 |
| B0000004 | 00040 | analyzerB4 | Ver.02 | Ver.02 | Ver.02 |
| | | | Ver.01 | Ver.01 | Ver.01 |

NEW PROGRAM IS PROVIDED.
DO YOU USE NEW PROGRAM?

520

YES — 521

| LOGIN ID | PASSWORD | COUNTRY NAME | LANGUAGE | DOWNLOAD TARGET | |
|---|---|---|---|---|---|
| | | | | PROGRAM | MANUAL |
| user01 | ******** | JPN | JPN | PROGRAM | MANUAL |

FIG. 10B

| PS CODE | SERIAL NUMBER | DOWNLOAD LIST | |
|---|---|---|---|
| | | PROGRAM VERSION | MANUAL VERSION |
| A0000001 | 00012 | Ver.03 | Ver.03_jpn |
| A0000001 | 00013 | Ver.03 | Ver.03_jpn |

FIG. 10C

| PS CODE | SERIAL NUMBER | DOWNLOAD FILE | |
|---|---|---|---|
| | | PROGRAM | MANUAL |
| A0000001 | 00012 | Ver.03 | Ver.03 |
| A0000001 | 00013 | Ver.03 | Ver.03 |

FIG. 10D

ANALYZER INFORMATION OF INFORMATION PROCESSOR AFTER UPDATE

| ANALYZER | PS CODE | SERIAL NUMBER | DEVICE NAME | EXECUTION VERSION | | | | HOLDING VERSION | | |
|---|---|---|---|---|---|---|---|---|---|---|
| | | | | PROGRAM VERSION | MANUAL | PROGRAM | MANUAL | PROGRAM VERSION | PROGRAM | MANUAL |
| FIRST ANALYZER | A0000001 | 00012 | analyzerA1 | Ver.03 | Ver.03 | Ver.03 | | | | |
| SECOND ANALYZER | A0000001 | 00013 | analyzerA2 | Ver.03 | Ver.03 | Ver.03 | | | | |
| THIRD ANALYZER | B0000004 | 00040 | analyzerB4 | Ver.02 | Ver.02 | Ver.02 | | | | |

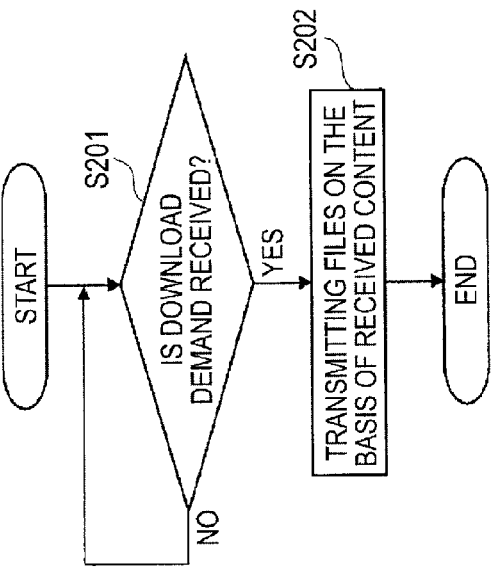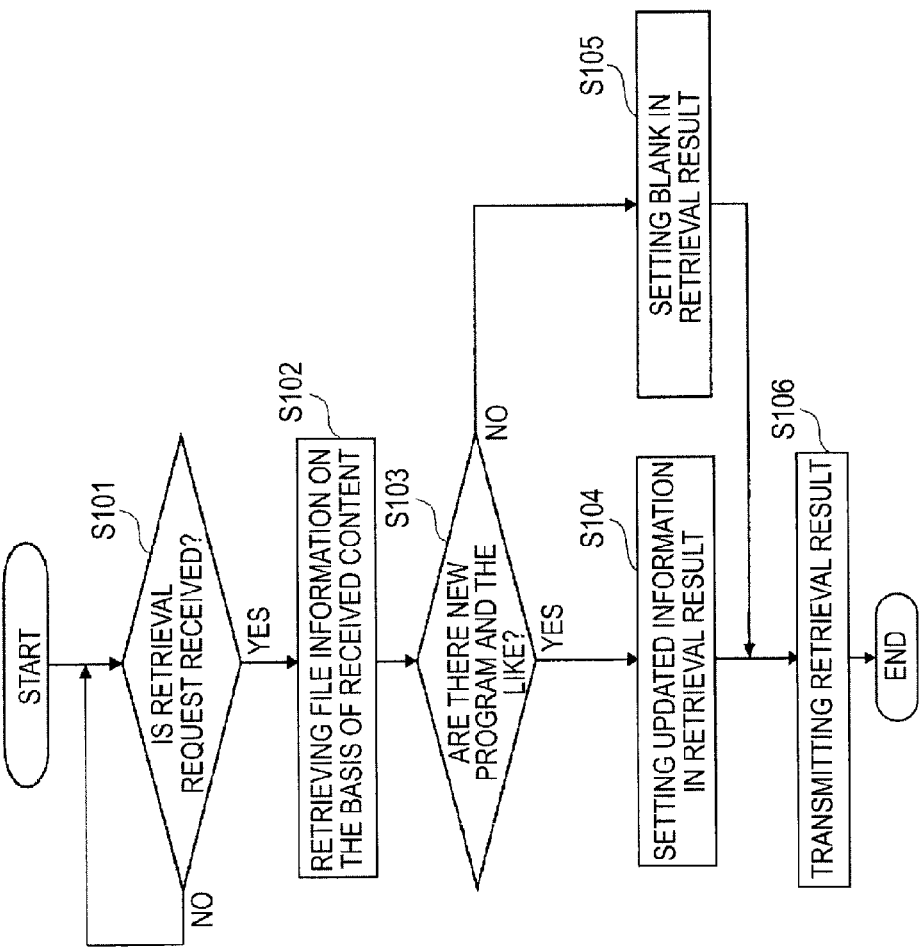

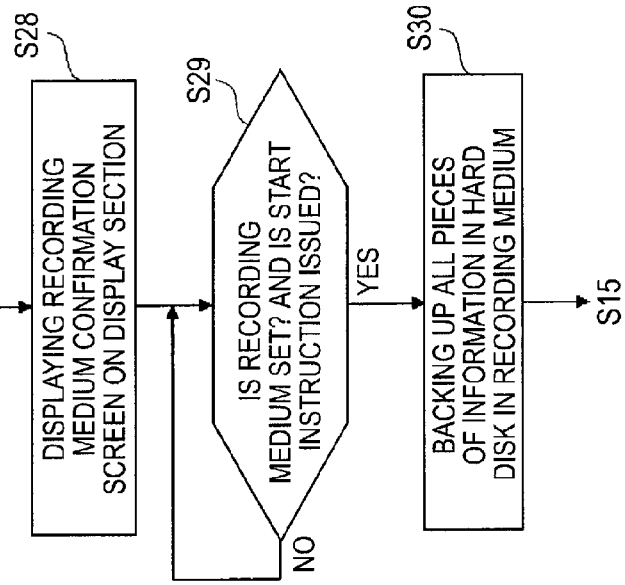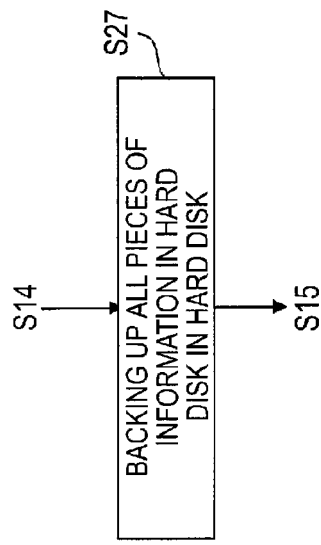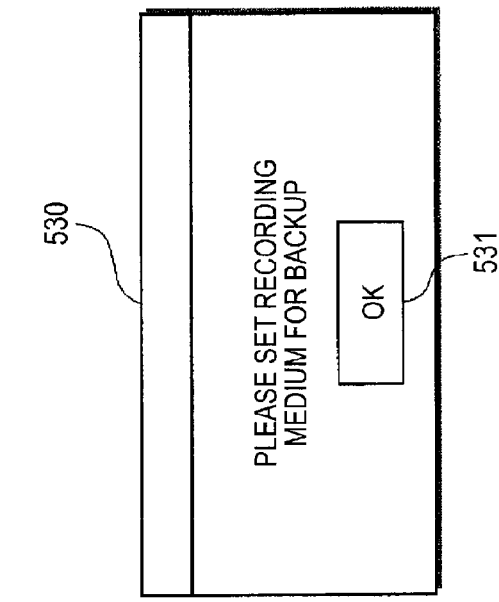

SAMPLE ANALYZING SYSTEM, SAMPLE ANALYZER AND MANAGEMENT APPARATUS

RELATED APPLICATIONS

This application claims priority under 35 U.S.C. §119 to Japanese Patent Application No. 2010-214540 filed on Sep. 24, 2010, the entire content of which is hereby incorporated by reference.

BACKGROUND OF THE INVENTION

1. Field of the Invention

The present invention relates to a sample analyzer which analyzes a sample, a management apparatus which is connected to the sample analyzer via the network, and a sample analyzing system which is provided with the sample analyzer and the management apparatus.

2. Description of the Related Art

Conventionally, there have been known sample analyzers which are connected to a server via a communication network so as to communicate therewith.

For example, Japanese Patent Publication No. 2009-85885 discloses a system in which a server which is connected to an automatic analyzer via a communication network so as to communicate therewith extracts a computer program requiring version upgrade on the basis of version information of the computer program received from the automatic analyzer and transmits this extracted computer program to the automatic analyzer.

In a clinical laboratory in which the above-described sample analyzer is disposed, it is desirable to install a manual corresponding to a version of a computer program controlling the sample analyzer so that a user can appropriately use the sample analyzer. However, in the system described in the above-described Japanese Patent Publication No. 2009-85885, when the version of the computer program of the automatic analyzer is upgraded, a service engineer is required to bring and install a manual corresponding to the computer program after version upgrade in the clinical laboratory, and the burden on the service engineer increases.

The invention is contrived in view of the demand, and an object thereof is to provide a sample analyzing system, a sample analyzer and a management apparatus which can reduce the burden on a service engineer with regard to the installation of a manual in the clinical laboratory.

SUMMARY OF THE INVENTION

The scope of the present invention is defined solely by the appended claims, and is not affected to any degree by the statements within this summary.

A first aspect of the present invention is a sample analyzing system, comprising: a sample analyzer configured to analyze a sample; and a management apparatus connected to the sample analyzer via a communication network, wherein the management apparatus comprises: a first memory that stores a computer program for the sample analyzer and manual data which corresponds to a version of the computer program and describes an operation procedure of the sample analyzer; a first communication device configured to communicate with the sample analyzer; and a first controller configured to transmit, via the first communication device to the sample analyzer, the computer program and the manual data corresponding to the version of the computer program which are stored in the first memory, and the sample analyzer comprises: a second communication device configured to communicate with the first communication device and to receive the computer program and the manual data transmitted from the first communication device; a second memory that stores the computer program and the manual data received by the second communication device; and a second controller configured to execute the computer program stored in the second memory.

A second aspect of the present invention is a sample analyzer which is connected to a management apparatus via a communication network, comprising: a receiving device configured to receive, from the management apparatus, a computer program and manual data which corresponds to a version of the computer program and describes an operation procedure of the sample analyzer; a memory that stores the computer program and the manual data received by the receiving device; and a controller configured to execute the computer program stored in the memory.

A third aspect of the present invention is a management apparatus which is connected to a sample analyzer via a communication network, comprising: a memory that stores a computer program for the sample analyzer and manual data which corresponds to a version of the computer program and describes an operation procedure of the sample analyzer; a transmission device; and a controller configured to transmit the computer program and the manual data corresponding to the version of the computer program which are stored in the memory to the sample analyzer via the transmission device.

BRIEF DESCRIPTION OF THE DRAWINGS

FIG. 5 is a diagram conceptually showing an example of file information according to the embodiment.

FIG. 6A is a diagram conceptually showing an example of setting information according to the embodiment, and FIG. 6B is a diagram showing a setting screen for setting information.

FIGS. 7A and 7B are diagrams each conceptually showing an example of analyzer information according to the embodiment.

FIG. 9A is a diagram showing a use instruction screen according to the embodiment, and FIG. 9B is a diagram conceptually showing an example of storage information.

FIG. 10A is a diagram conceptually showing an example of a part of setting information according to the embodiment, FIG. 10B is a diagram conceptually showing an example of a retrieval result, FIG. 10C is a diagram conceptually showing an example of the content of a download demand, and FIG. 10D is a diagram conceptually showing an example of the state of analyzer information.

FIG. 11A is a flowchart showing a process using the management apparatus when receiving a retrieval request according to the embodiment, and FIG. 11B is a flowchart showing a process using the management apparatus when receiving a download demand.

FIGS. 12A and 12B are flowcharts showing a backup process according to a modified example of the embodiment, and FIG. 12C is a diagram showing a recording medium confirmation screen.

DETAILED DESCRIPTION OF THE PREFERRED EMBODIMENTS

The advantageous effects and the purpose of the invention will become further obvious through the following descriptions of the embodiments. However, the following embodiments are an example when implementing the invention, and the invention is not limited to the following embodiments.

This embodiment relates to a sample analyzing system for performing blood examination and analysis to which the invention is applied. The sample analyzing system according to this embodiment is provided with a sample analyzer including one information processor and three analyzers. In the three analyzers, blood analysis is performed in parallel and the measurement result is transmitted to the information processor.

Hereinafter, the sample analyzing system according to this embodiment will be described with reference to the drawings.

Figure 1:
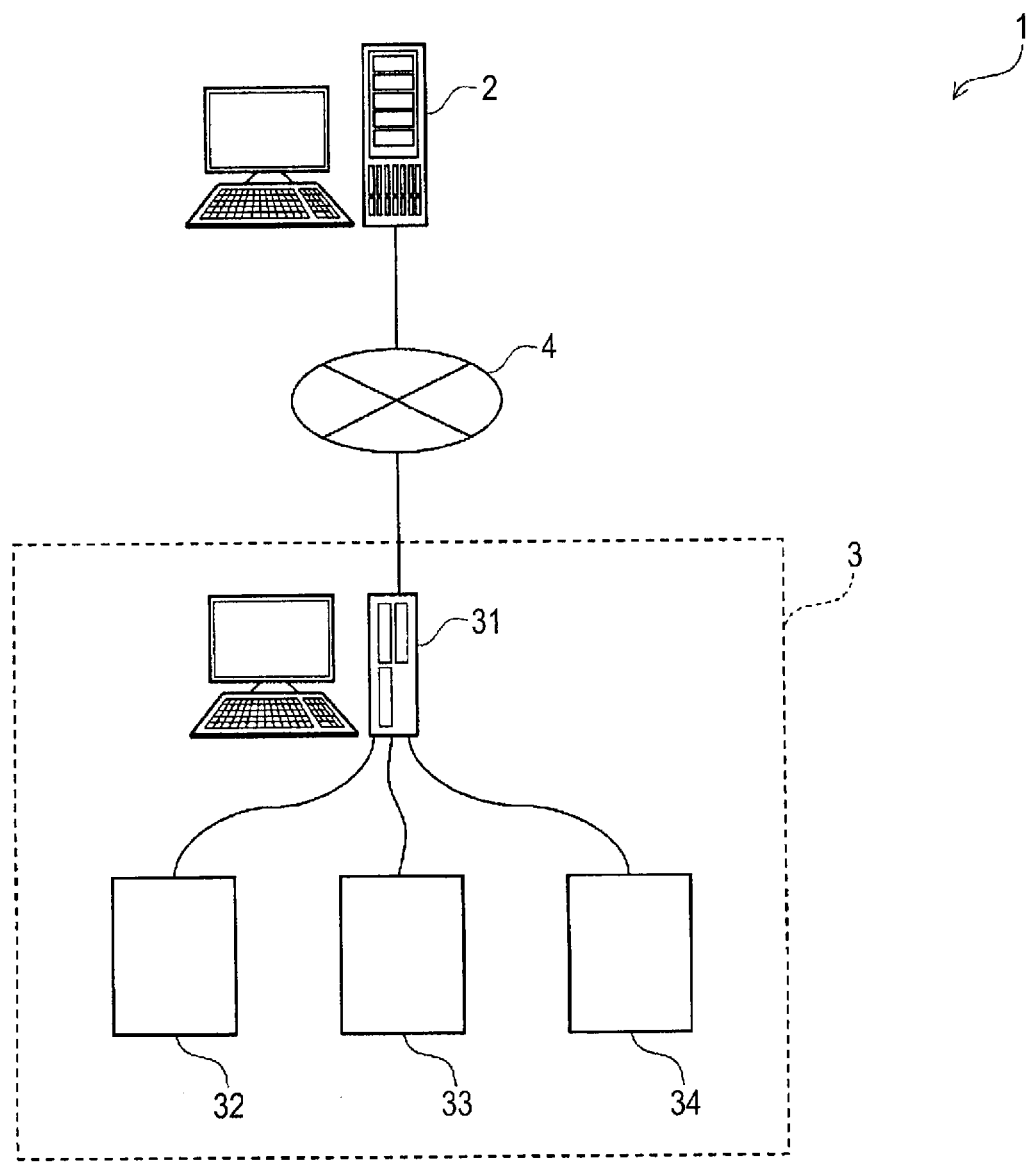
FIG. 1 is a diagram showing the configuration of a sample analyzing system according to an embodiment.

FIG. 1 is a diagram showing the configuration of a sample analyzing system 1. As shown in the drawing, the sample analyzing system 1 according to this embodiment includes a management apparatus 2 and a sample analyzer 3. The management apparatus 2 and the sample analyzer 3 are connected to each other via a network 4 constituted by the internet or a dedicated line so as to perform communication therebetween.

The sample analyzer 3 is provided with an information processor 31 and analyzers 32 to 34. The information processor 31 is connected to each of the analyzers 32 to 34 so as to communicate therewith. The information processor 31 controls the analyzers 32 to 34 and receives sample measurement results from the analyzers 32 to 34. When the information processor 31 is powered up, the analyzers 32 to 34 enter a startup state.

Figure 2:
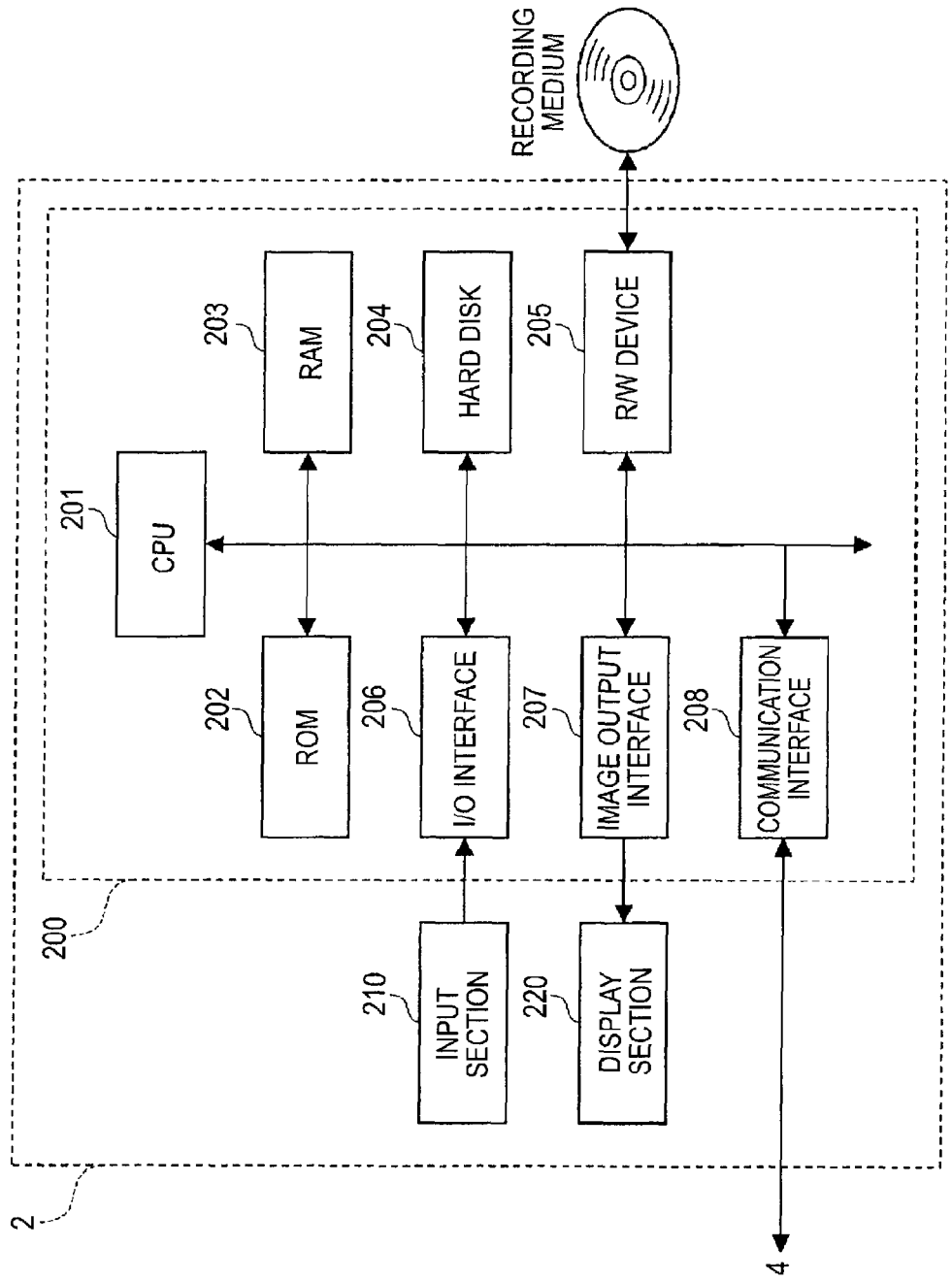
FIG. 2 is a diagram showing the configuration of a management apparatus according to the embodiment.

FIG. 2 is a diagram showing the configuration of the management apparatus 2.

The management apparatus 2 is configured to have a main body 200, an input section 210, and a display section 220. The main body 200 has a CPU 201, a ROM 202, a RAM 203, a hard disk 204, an R/W device 205, an I/O interface 206, an image output interface 207, and a communication interface 208.

The CPU 201 executes computer program which are stored in the ROM 202 and computer programs which are loaded to the RAM 203. The RAM 203 is used to read out computer programs which are recorded in the ROM 202 and the hard disk 204. In addition, the RAM 203 is also used as a working area of the CPU 201 when these computer programs are executed.

The hard disk 204 stores various computer programs to be executed in the CPU 201, such as an operating system and application programs, and data which is used in execution of the computer programs. In addition, the hard disk 204 stores information (hereinafter, referred to as "file information") including a computer program which is executed in the information processor 31 and manual data (hereinafter, referred to as "electronic manual") corresponding to this computer program. The file information will be described later with reference to FIG. 5. In addition, the electronic manual will also be described later.

The R/W device 205 is configured to have a floppy (registered trademark)-disk drive, a CD drive, a DVD drive or the like, can read out a computer program and data recorded in a recording medium, and can write a computer program and data in these recording mediums.

The I/O interface 206 is connected to the input section 210 formed of a mouse or a keyboard. The image output interface 207 is connected to the display section 220 configured to have a display or the like, and outputs a video signal according to image data to the display section 220. The display section 220 displays an image on the basis of the input video signal. The communication interface 208 is connected to the network 4. Accordingly, data transmission and reception between the management apparatus 2 and the sample analyzer 3 can be performed.

Figure 3:
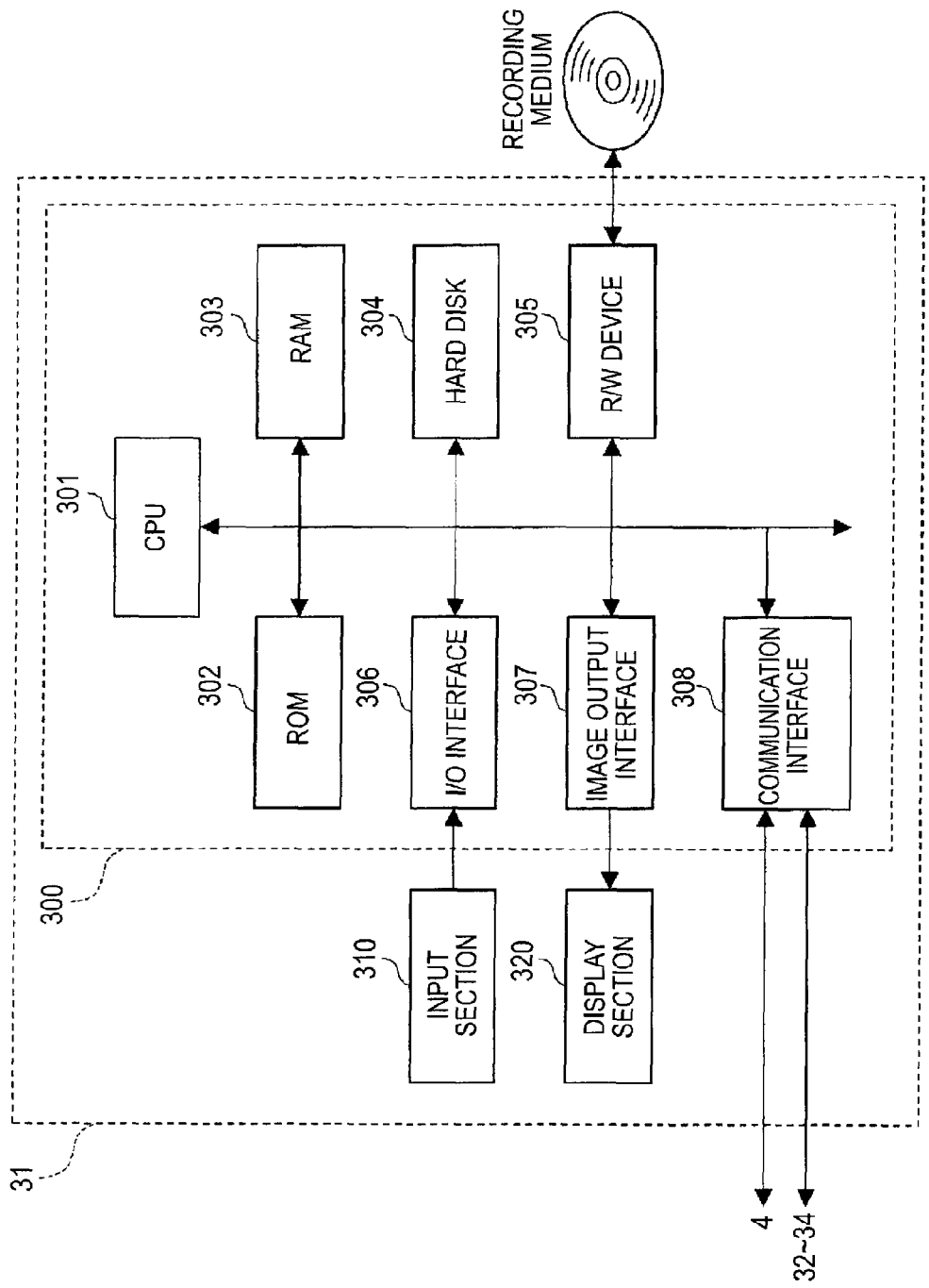
FIG. 3 is a diagram showing the configuration of an information processor according to the embodiment.

FIG. 3 is a diagram showing the configuration of the information processor 31.

The information processor 31 has the same configuration as that of the management apparatus 2 and is thus configured to have a main body 300, an input section 310, and a display section 320. The main body 300 has a CPU 301, a ROM 302, a RAM 303, a hard disk 304, an R/W device 305, an I/O interface 306, an image output interface 307, and a communication interface 308.

The hard disk 304 of the information processor 31 stores various computer programs to be executed in the CPU 301, such as an operating system and application programs, and data which is used in execution of the computer programs.

In addition, the hard disk 304 stores information (hereinafter, referred to as "setting information") related to the setting of the information processor 31. In addition, the hard disk 304 stores information (hereinafter, referred to as "analyzer information") including computer programs for controlling the analyzers 32 to 34 and electronic manual or the like corresponding to these computer programs. In addition, the hard disk 304 stores information (hereinafter, referred to as "storage information") including computer programs which were used in the past to control the analyzers 32 to 34 and electronic manuals or the like corresponding to these computer programs. The setting information, the analyzer information, and the storage information will be described later with reference to FIGS. 6A, 7A, 7B, and 9B.

Since the constituent parts other than the hard disk 304 have the same configuration as in the management apparatus 2, descriptions thereof will be omitted.

Figure 4:
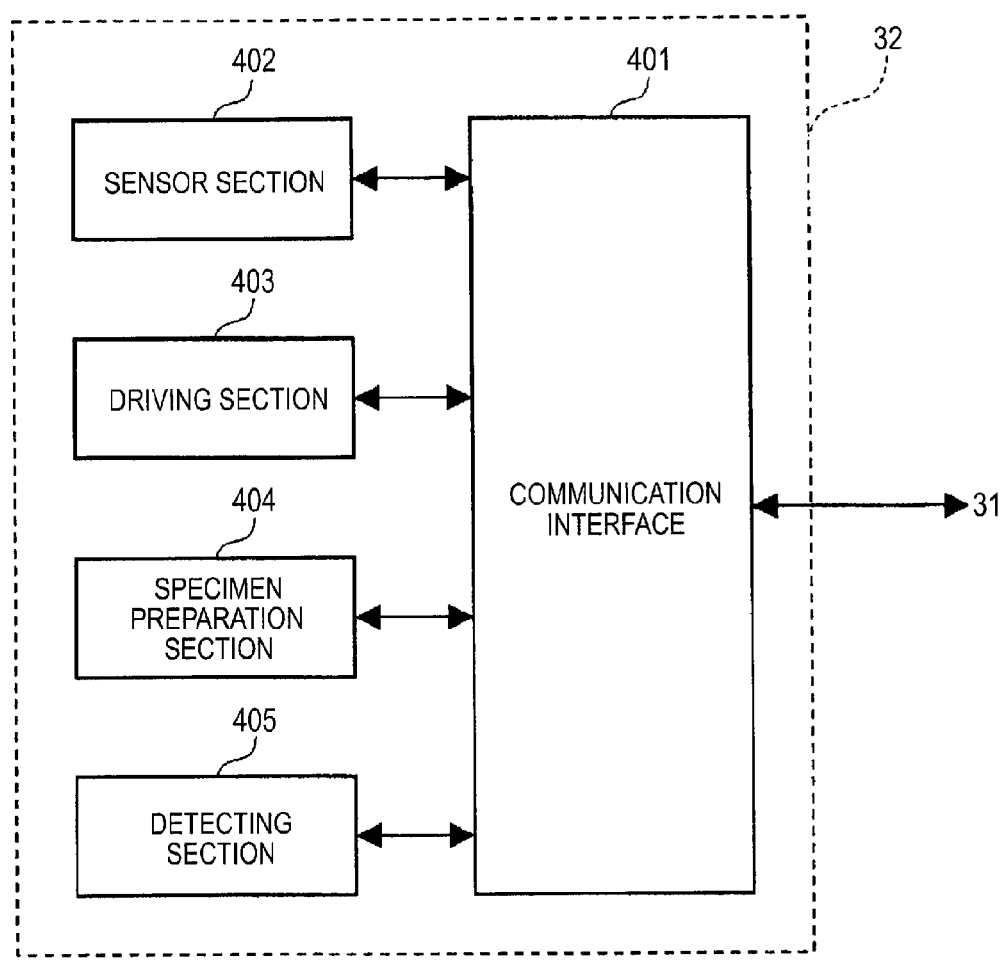
FIG. 4 is a diagram showing the configuration of an analyzer according to the embodiment.

FIG. 4 is a diagram showing the configuration of the analyzer 32. Since the analyzers 32 to 34 have almost the same configuration, only the configuration of the analyzer 32 will be described for the sake of convenience.

The analyzer 32 is configured to have a communication interface 401, a sensor section 402, a driving section 403, a specimen preparation section 404, and a detecting section 405.

The communication interface 401 performs data communication with the communication interface 308 of the information processor 31. The sensor section 402 includes a sensor installed in the analyzer 32. The driving section 403 includes a mechanism for driving the sections in the analyzer 32. The specimen preparation section 404 prepares a specimen for measurement using a sample and a reagent. The detecting section 405 measures a specimen prepared by the specimen preparation section 404.

The sensor section 402, the driving section 403, the specimen preparation section 404, and the detecting section 405 are controlled by the CPU 301 of the information processor 31 via the communication interface 401. In addition, a detection signal of the sensor section 402 and a measurement result by the detecting section 405 are transmitted to the information processor 31 via the communication interface 401.

FIG. 5 is a diagram conceptually showing an example of file information which is stored in the hard disk 204 of the management apparatus 2.

The file information has a PS code type item, a version item, a region item, a program item, a language item, and a manual item.

In the PS code type item, the PS code type of the analyzer is stored. That is, a PS code (for example, "A0000001", "B0000004" or the like) showing the type is adhered to the analyzer, and in the PS code type item, the type of the PS code (for example, "PS code A type" or "PS code B type") is stored.

In the version item, the version of a computer program (hereinafter, referred to as "program") in the program item and the version of an electronic manual in the manual item are stored. In the region item, the region in which a program in the program item is used is stored. In the program item, the program (data) which is executed on the information processor 31 and is used in the control of the analyzer is stored. Each program is stored corresponding to a country name in the region item. In the language item, the language which is used in an electronic manual in the manual item is stored. In the manual item, the electronic manual for a corresponding version of a program is stored.

In the electronic manual of this embodiment, an operation procedure of a program which is executed on the information processor 31 and is used in the control of the analyzer, that is, an operation procedure of the sample analyzer 3 based on the program is written. This electronic manual is a PDF file, in which the operation procedure of the analyzer is written according to the page number as in a manual having a booklet format, and is written for each of the paragraphs such as chapters, clauses, and items. When a user does not know a program operation, the user refers to a corresponding section in this electronic manual. This electronic manual is not incorporated in a part of the program, but is a data file independent from the program. A user can create a manual having a booklet format by printing out this electronic manual.

Here, in the file information shown as an example in FIG. 5, all the versions (1 to 3) of the programs which are used in the control of the analyzers of which the PS code is the A type are stored. Regarding these programs, the larger the version number is, the newer program is. That is, in the example in FIG. 5, the version 3 of the program is the newest, and the version 1 of the program is the oldest. The respective versions of the programs are provided corresponding to regions such as Japan, America, and the like. In addition, electronic manuals written in a plurality of languages are stored corresponding to the respective versions of the programs. In addition, in the file information, information for use in the control of an analyzer of which the PS code is not the A type is also stored as in the information related to the analyzer of which the PS code is the A type.

The programs, the electronic manuals and the like which are stored in the file information of the management apparatus 2 are appropriately transmitted to the information processor 31 by the communication between the management apparatus 2 and the information processor 31 as described later.

FIG. 6A is a diagram conceptually showing an example of setting information which is stored in the hard disk 304 of the information processor 31.

The setting information has a login ID item, a password item, a country name item, a language item, a download target item, and a download setting item.

In the login ID item and the password item, a letter string which is used when the information processor 31 accesses the management apparatus 2 is stored. In the country name item and the language item, the name of a country in which the sample analyzer 3 including the information processor 31 is installed, and the used language are stored, respectively. In the download target item, the type of a file which is downloaded from the management apparatus 2 is stored. In the download target item of this embodiment, the "program" and the "manual" are fixed.

In the download setting item, whether the download from the management apparatus 2 is performed automatically or manually is stored. When the setting information is set as shown in FIG. 6A, the information processor 31 automatically downloads a program for controlling the analyzer and an electronic manual corresponding to this program from the management apparatus 2.

FIG. 6B is a diagram showing a setting screen 510 for setting information, which is displayed on the display section 320 of the information processor 31.

The setting screen 510 is provided with an automatic download setting area 511, a main body information setting area 512, an OK button 513, and a cancel button 514.

The automatic download setting area 511 has buttons to select either of "automatic" or "manual". When a user presses any one of the buttons, the pressed button is selected.

The main body information setting area 512 has selection lists 512a and 512b and input areas 512c and 512d. A user can select the country name and the language from the selection lists 512a and 512b, respectively, and a user ID and a password can be input to the input areas 512c and 512d, respectively.

When a user presses the OK button 513, the contents in the automatic download setting area 511 and the main body information setting area 512 are overwritten on the setting information of the information processor 31. In addition, when a user presses the cancel button 514, the contents which are newly set on the setting screen 510 are discarded.

FIG. 7A is a diagram conceptually showing an example of analyzer information which is stored in the hard disk 304 of the information processor 31.

The analyzer information has an analyzer item, a PS code item, a serial number item, a device name item, an execution version item, and a holding version item. Both of the execution version item and the holding version item have a program version item, a program item, and a manual item.

In the analyzer item, the PS code item, the serial number item, and the device name item, the identification number (order of arrangement) of the analyzer connected to the information processor 31, the PS code, the serial number, and the device name are written, respectively. These items are set in advance in this analyzer information when the analyzer is connected to the information processor 31. The PS code is a code showing the analyzer type as described above, and the serial number is a number corresponding to the manufacture's serial number in the PS code.

In the execution version item, the version of a program which is used at the present time, the program which is used at the present time, and the electronic manual which is used at the present time are stored. That is, when the analyzer information is set as shown in FIG. 7A, the information processor 31 uses a version 2 of a program of which the PS code is the A type when driving the first and second analyzers at the present time. In addition, an electronic manual corresponding to this program can be accessed by a user. Similarly, the information processor 31 uses a version 2 of a program of which the PS code is the B type when driving the third analyzer at the present time. In addition, an electronic manual corresponding to this program can be accessed by a user. When the display section 320 of the information processor 31 displays an electronic manual, a user can change a section to be displayed by scrolling the electronic manual.

In the holding version item, the version of a program which is downloaded from the management apparatus 2, the program which is downloaded from the management apparatus 2, and the electronic manual which is downloaded from the management apparatus 2 are stored. In FIG. 7A, the holding version item is blank.

When a program, an electronic manual and the like are downloaded from the management apparatus 2 by the information processor 31 from the state of the analyzer information shown in FIG. 7A, the state of the analyzer information becomes as shown in FIG. 7B. That is, as shown by the broken line part in FIG. 7B, a version 3 of a program for driving the first and second analyzers is stored in the program item in the holding version item. In addition, an electronic manual corresponding to this program is stored in the manual item in the holding version item. Here, a new program for driving the third analyzer is not downloaded. In this case, as shown in the drawing, the items in the holding version item corresponding to the third analyzer are blank.

Figure 8:
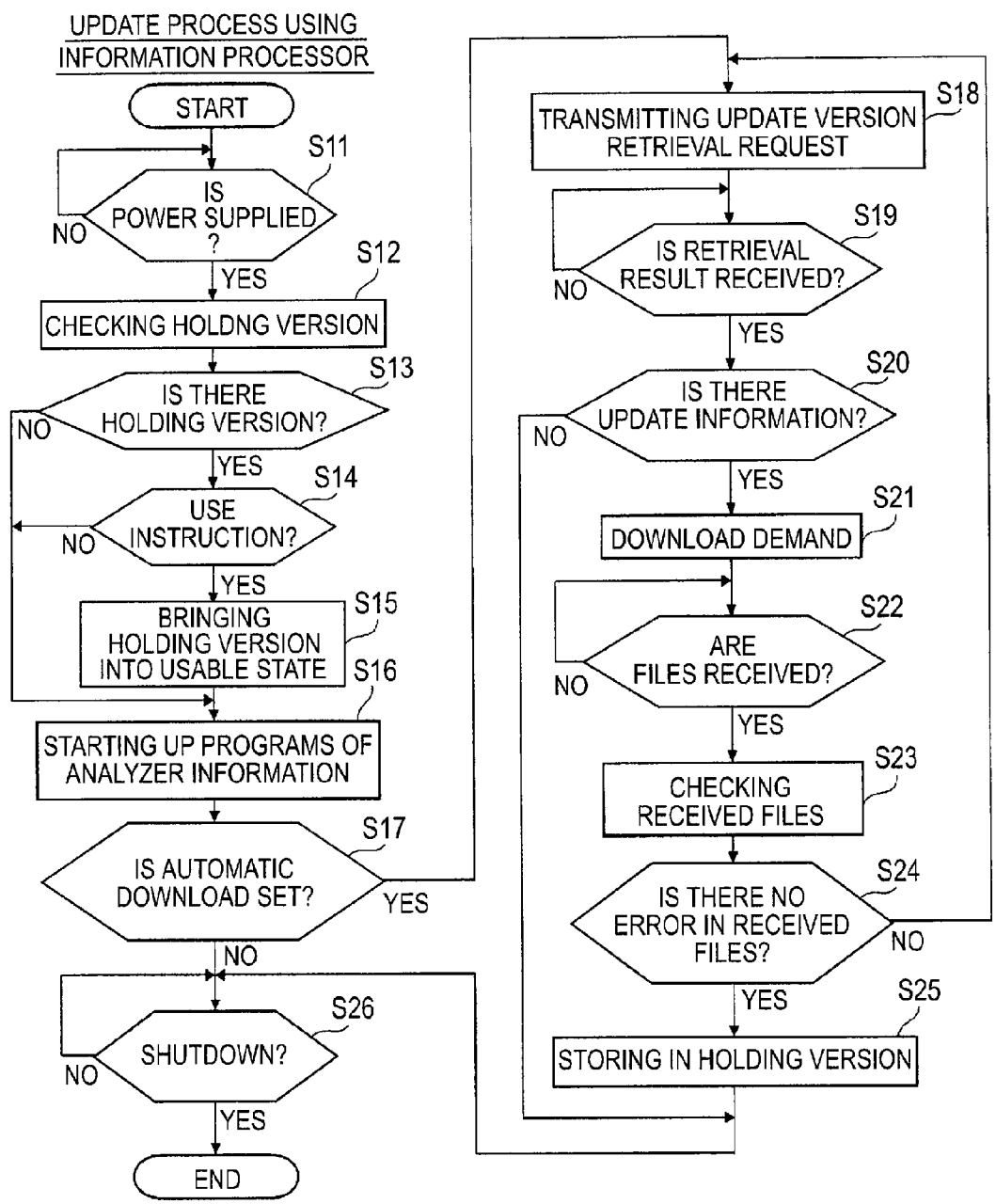
FIG. 8 is a flowchart showing an update process using the information processor according to the embodiment.

FIG. 8 is a flowchart showing an update process using the information processor 31.

When receiving a power supply instruction by a user (S11: YES), the CPU 301 of the information processor 31 checks a holding version of the analyzer information (S12). Next, the CPU 301 determines the presence or absence of the holding version (S13). That is, when all the items in the holding version of the analyzer information are blank as shown in FIG. 7A, the CPU 301 determines that there is no holding version, and when the items in the holding version of the analyzer information are not blank as shown in FIG. 7B, the CPU 301 determines that there is a holding version.

When determining that there is a holding version (S13: YES), the CPU 301 displays a use instruction screen 520 on the display section 320 and determines whether or not an instruction has been issued by a user to use the holding version (S14). On the other hand, when the CPU 301 determines that there is no holding version (S13: NO), the process proceeds to S16.

FIG. 9A is a diagram showing the use instruction screen 520 which is displayed on the display section 320 of the information processor 31.

The use instruction screen 520 is provided with an OK button 521 and a cancel button 522. When a user presses the OK button 521, an instruction is transmitted to the CPU 301 of the information processor 31 to use the holding version. In addition, when a user presses the cancel button 522, an instruction is transmitted to the CPU 301 of the information processor 31 so as not to use the holding version.

Returning to FIG. 8, when receiving the use instruction due to the pressed OK button 521 of the use instruction screen 520 (S14: YES), the CPU 301 of the information processor 31 brings holding version of programs and the like into a usable state (S15). That is, first, the CPU 301 adds programs and the like of the items of the execution version to the corresponding items of a storage version in storage information (see FIG. 9B) to be described later. Then, the CPU 301 overwrites the programs and the like of the items of the holding version on the corresponding items of the execution version in the analyzer information. On the other hand, due to the pressed cancel button 522 of the use instruction screen 520, when the CPU 301 receives an instruction so as not to use the holding version of the program and the like (S14: NO), the process proceeds to S16.

FIG. 9B is a diagram conceptually showing an example of storage information which is stored in the hard disk 304 of the information processor 31.

The storage information has a PS code item, a serial number item, a device name item, and a storage version item. The storage version item has a program version item, a program item, and a manual item. The PS code item, the serial number item, the device name item, the program version item, the program item, and the manual item in the storage information are the same as in the analyzer information.

As shown in the drawing, all the programs and the like which were stored in the execution version item in the analyzer information in the past are stored in the storage version item in the storage information. In the process of S15 in FIG. 8, when the programs and the like of the execution version are added to the storage information, the program version, the program, and the electronic manual of the execution version item are stored in an area in which the PS code, the serial number, and the device name are matched. Accordingly, for example, even when there is a problem in the programs of the execution version item, it is possible to appropriately return the programs of a version which is stored in the storage version to a usable state.

Returning to FIG. 8, the CPU 301 of the information processor 31 starts up the programs of the execution version item in the analyzer information (S16). Accordingly, the analyzers 32 to 34 are driven by the information processor 31, and measurement operations by the analyzers 32 to 34 are started. The measurement operations of the analyzers 32 to 34 are performed in parallel to the following processes of S17 to S25.

Next, The CPU 301 determines whether or not the automatic download item in the setting information is set to be in an automatic mode (S17). When the automatic download item is set to be in a manual mode (S17: NO), the process proceeds to S26 and the process such as the measurement is continuously performed until the information processor 31 is shut down (S26). On the other hand, when the automatic download item is set to be in an automatic mode (S17: YES), the CPU 301 transmits an update version retrieval request to the management apparatus 2 (S18).

Here, the retrieval request which is transmitted to the management apparatus 2 from the information processor 31 includes the information shown in FIG. 10A and the analyzer information shown in FIG. 7A or 7B. The information in FIG. 10A is formed of the items in the setting information in FIG. 6A, excluding the download setting.

FIG. 11A is a flowchart showing a process using the management apparatus 2 when receiving the update version retrieval request from the information processor 31.

When receiving the retrieval request from the information processor 31 (S101: YES), the CPU 201 of the imaging apparatus 2 retrieves the file information on the basis of the content of the retrieval request (S102). In greater detail, the CPU 201 retrieves whether or not there is a newer version than the execution version and the holding version included in the retrieval request in the version item in the file information which matches the PS code item included in the content of the retrieval request.

When there is a new version of a program (S103: YES), the version of the program found by the retrieval and the version of the electronic manual are set in the download list item of the retrieval result shown in FIG. 10B (S104). In place of the program version and electronic manual version, a file name of the program and a file name of the electronic manual may be set. Next, the CPU 201 transmits the retrieval result shown in FIG. 10B to the information processor 31 (S106).

On the other hand, when there is no new version of a program and the like (S103: NO), a blank is set in the download item of the retrieval result (S105). Next, the CPU 201 transmits the retrieval result in which the download item is blank in FIG. 10B to the information processor 31 (S106).

When the information processor 31 is newly installed, the execution version item and the holding version item which are included in the retrieval request received by the management apparatus 2 are all blank. In this case, the CPU 201 transmits the newest version of a program in the file information to the information processor 31.

Returning to FIG. 8, when receiving the retrieval result from the management apparatus 2 (S19: YES), the CPU 301 of the information processor 31 determines whether there is update information about the program of the analyzer on the basis of the received retrieval result (S20). That is, when the download item of the received retrieval result is all blank, it is determined that there is no update information (S20: NO) and the process proceeds to S26. On the other hand, when the download item of the received retrieval result is not all blank, it is determined that there is update information (S20: YES) and the process proceeds to S21.

When there is update information, the CPU 301 transmits a download demand including a part of the setting information shown in FIG. 10A and the retrieval result received in S19 to the management apparatus 2 (S21).

FIG. 11B is a flowchart showing a process using the management apparatus 2 when the download demand is received from the information processor 31.

When receiving the download demand from the information processor 31 (S201: YES), the CPU 201 of the management apparatus 2 transmits files on the basis of the content of the download request (S202). That is, on the basis of the program version and the electronic manual version of the download list item included in the download demand, the PS code, the serial number, the program (data) and the electronic manual are transmitted to the information processor 31 by a single transmission procedure as shown in FIG. 10C. Accordingly, the program and the electronic manual are received by the information processor 31 at the same time.

In addition, on the basis of the country name which is included in the download demand received from the information processor 31, a program for a corresponding region is transmitted to the information processor 31. In addition, on the basis of the language which is included in the download demand received from the information processor 31, an electronic manual of a manual in a corresponding language is transmitted to the information processor 31.

Returning to FIG. 8, when receiving the program, the electronic manual and the like from the management apparatus 2 (S22: YES), the CPU 301 of the information processor 31 checks the received files (S23). In greater detail, first, the CPU 301 of the information processor 31 transmits a CRC code generated from the received files to the management apparatus 2. The CPU 201 of the management apparatus 2 compares the CRC code generated from the transmitted files with the CRC code received from the information processor 31 to determine whether or not there is an error in the file transmission, and transmits the determination result to the information processor 31.

When determining that there is no error in the downloaded files on the basis of the determination result which is received from the management apparatus 2 (S24: YES), the CPU 301 stores the received files and the like in the holding version item (S25). On the other hand, when it is determined that there is an error in the downloaded files (S24: NO), the process returns to S18 and the CPU 310 repeats the processes of S19 to S24 until receiving normal files. In this manner, when normal files are received, the process proceeds to S26 and the process such as the measurement is continuously performed until the information processor 31 is shut down (S26).

In this manner, in the case in which the update process using the information processor 31 is performed, when the analyzer information is as shown in FIG. 7A at the time of the supply of power to the information processor 31, a new version of a program and an electronic manual are transmitted from the management apparatus 2 when the automatic download is set to be in an automatic mode, and the analyzer information becomes as shown in FIG. 7B. Thereafter, when the information processor 31 is shut down and re-started up, due to the analyzer information which is as shown in FIG. 7B, an update instruction is received from a user by the screen in FIG. 9A, and thus the programs and the like of the holding version item are overwritten on the execution version items. Accordingly, the analyzer information becomes as shown in FIG. 10D, and a new version of a program and an electronic manual can be used.

According to this embodiment, when a new version of a program is transmitted to the information processor 31, an electronic manual corresponding to this program is transmitted together. Accordingly, a service engineer is not required to separately bring a manual corresponding to the program after version upgrade up to a position at which the sample analyzer 3 (information processor 31) is installed. Therefore, the burden on the service engineer can be reduced.

In addition, according to this embodiment, the programs and the electronic manuals of the execution version item are added (backup) to the storage version item in the storage information before the programs and the electronic manuals of the holding version item are overwritten on the execution version item. Accordingly, even when a problem occurs during the use of the program of the execution version item, an old version of a program and an electronic manual are easily used again as the execution version.

In addition, according to this embodiment, when the sample analyzer 3 (information processor 31) is powered up, the programs and the electronic manuals in the holding version item are overwritten on the execution version item, and then the programs of the information processor 31 are executed. Accordingly, the analyzers 32 to 34 can be controlled by the new versions of the programs. In addition, since the programs and the electronic manuals in the holding version item are overwritten on the execution version item only when the sample analyzer 3 (information processor 31) is powered up, it is possible to prevent the analysis conditions from changing due to a change of the program of the execution version item during, for example, the analysis operations of the analyzers 32 to 34. Not only when the sample analyzer 3 is powered up, but also during the power-OFF state of the sample analyzer 3, the programs and the electronic manuals in the holding version item may be overwritten on the execution version item.

In addition, according to this embodiment, by setting the download setting item in the setting information, it is possible to set whether or not a new version of a program and the like is automatically acquired. In addition, even in the setting in which a new version of a program and the like are automatically acquired, whether or not a new version of a program and the like are used is confirmed by a user by the screen shown in FIG. 9A. Accordingly, a new version of a program and the like are not overwritten on the execution version at an unintended timing for the user, and thus the user can continuously use the favorite version of the program.

In addition, according to this embodiment, the electronic manual is not incorporated in a part of the computer program and transmitted to the information processor 31, but is transmitted to the information processor 31 as a data file independent from the computer program. Therefore, for example, when the electronic manual is partially revised, only the electronic manual can be revised and transmitted again to the information processor 31 without requiring an effort such as the modification of the computer program itself incorporated with the electronic manual.

In addition, in the case in which the electronic manual is incorporated in a part of the computer program, for example, when an error occurs in the sample analyzer 3, the computer program is not excellently operated due to the error, and thus there is concern that the electronic manual cannot be displayed on the display section 320. However, in this embodiment, the electronic manual and the computer program exist as different files, and thus even when the computer program is not excellently operated, a user can refer to the electronic manual.

In addition, in this embodiment, a manual having a booklet format can be easily made by printing out the electronic manual. Accordingly, even when the electronic manual cannot be displayed on the display section 320 due to an error occurring in the sample analyzer 3, a user can deal with the error with reference to the manual having a booklet format. In addition, an analyzer at a position remote from the display section 320 can be operated with reference to the manual.

The embodiments of the invention have been described, but the invention is not limited to the above-described embodiments. In addition, various modifications other than the above description can be made in the embodiments of the invention.

For example, in the above-described embodiments, blood is exemplified as a measurement target. However, urine may be a measurement target. That is, the invention can also be applied to sample processing systems which examine urine and can be further applied to clinical sample processing systems which examine other clinical samples.

In addition, in the above-described embodiments, the program and the electronic manual are transmitted to the information processor 31 from the management apparatus 2 by a single transmission procedure using the management apparatus 2, and thus the program and the electronic manual are received by the information processor 31 at the same time. However, the invention is not limited thereto. The program and the electronic manual may be individually transmitted to the information processor 31 from the management apparatus 2 by two or more times of transmission procedures using the management apparatus 2, and thus the program and the electronic manual may be received by the information processor 31 at different timings. For example, after determination that there is no error in the program received by the information processor 31, the electronic manual may be received by the information processor 31. In addition, after determination that there is no error in the electronic manual received by the information processor 31, the program may be received by the information processor 31.

In addition, in the above-described embodiments, the program and the electronic manual may be transmitted as one file from the management apparatus 2. In this case, for example, the transmission content shown in FIG. 10C is transmitted in the form organized to one file. In addition, the program and the manual file may be transmitted as different files from the management apparatus 2. In this case, for example, the transmission content shown in FIG. 10C is transmitted to be included in the single transmission procedure using the management apparatus 2.

In addition, in the above-described embodiments, the program and the electronic manual are received by the information processor 31. However, the invention is not limited thereto, and the program and the electronic manual may be received by another download terminal in the sample analyzer 3, which is independent from the information processor 31. In addition, a terminal receiving the program and a terminal receiving the electronic manual may be different from each other.

In addition, in the above-described embodiments, the update version retrieval request is transmitted to the management apparatus 2 from the information processor 31, and the management apparatus 2 performs the retrieval of the update version. However, the invention is not limited thereto, and the retrieval of the update version may be performed by the information processor 31. In this case, all the versions in the respective PS code types stored in the management apparatus 2 may be transmitted to the information processor 31, and on the basis of this transmission content, the retrieval of a new version may be performed by the information processor 31. In addition, when all the versions of the programs in the respective PS code types stored in the management apparatus 2 are transmitted to the information processor 31 and compared with each other by the information processor 31, and thus the information processor 31 determines that there is a new version of a program, the program may be brought into a usable state on the information processor 31 and other programs may be discarded.

In addition, in the above-described embodiments, an electronic manual having a PDF format is transmitted to the information processor 31 from the management apparatus 2. However, the format is not limited to the PDF format, and an electronic manual having a WORD format, an EXCEL format or the like may be transmitted.

In addition, in the above-described embodiments, a section to be displayed can be changed by scrolling the electronic manual displayed on the display section 320 of the information processor 31 by a user, but the invention is not limited thereto. For example, in a help screen which is displayed at the time of occurrence of a trouble, when a user presses a display instruction button which is disposed in this help screen, only a section in which a method of dealing with this trouble is described among the electronic manuals which are stored in the information processor 31 may be displayed on the display section 320 of the information processor 31. That is, in the invention, a part which shows a method of handling a trouble and the like in the information described in the electronic manual may be presented to a user in any form.

In addition, in the above-described embodiments, the information processor 31 includes the versions of the execution version and the holding version in the retrieval request. However, the invention is not limited thereto, and information processor 31 may include the version of the storage version in the retrieval request. Accordingly, the management apparatus 2 can grasp all the versions stored in the information processor 31, and thus the program and the like can be efficiently transmitted.

In addition, in the above-described embodiments, when it is determined that there is a holding version in S13 in FIG. 8, the use instruction screen 520 in FIG. 9A is displayed, and whether or not a program of the holding version is brought into a usable state is determined by the OK button 521 and the cancel button 522. However, the invention is not limited thereto, and when it is determined that that there is a holding version, a holding version of a program may be automatically brought into a usable state. In this case, the information processor 31 is configured so that whether or not the holding version of the program is automatically brought into a usable state is set in advance by a user in the information processor 31.

In addition, in the above-described embodiments, when the holding version of the program is brought into a usable state in S15 in FIG. 8, the execution version of the program and the like are added to the storage information shown in FIG. 9B. However, the invention is not limited thereto, and the whole information (including setting information, analyzer information, measurement data and the like) stored in the information processor 31 may be backed up.

FIG. 12A is a flowchart showing a backup process using the information processor 31. S27 shown in FIG. 12A is inserted between S14 and S15 in FIG. 8.

When a user issues an instruction to use a holding version (S14: YES), the CPU 301 of the information processor 31 backs up all the information in the hard disk 304 to a predetermined location in the hard disk 304 (S27). Accordingly, for example, even when a problem occurs when the program of the holding version item is overwritten on the execution version, it is possible to return the information processor 31 to a state upon backup on the basis of the backup information in the hard disk 304.

In S27, the information in the hard disk 304 is backed up to the hard disk 304. However, the invention is not limited thereto, and the information may be stored in a recording medium. In this case, in place of S27 in FIG. 12A, S28 and S29 are inserted as shown in FIG. 12B.

First, referring to FIG. 12B, the CPU 301 of the information processor 31 displays a recording medium confirmation screen 530 as shown in FIG. 12C (S28). Next, the CPU 301 determines whether or not a recording medium is set in the R/W device 305 (see FIG. 3) by a user and an OK button 531 is pressed by the user (S29). When the recording medium is set and the OK button 531 is pressed (S29: YES), the CPU 301 backs up all the information in the hard disk 304 to the recording medium set in the R/W device 305 (S30). Also in this case, it is possible to return the information processor 31 to a state upon backup on the basis of the backup information in the recording medium.

In addition, in the above-described embodiments, in the download target item shown in FIG. 6A, the "program" and the "manual" are fixed. However, the invention is not limited thereto, and other files may be included. In addition, the download target item may be appropriately set by a user.

In addition, in the above-described embodiments, the language which is used by a user in the information processor 31 is stored in the hard disk 304 (setting information) in the information processor 31. However, the invention is not limited thereto, and the language may be stored in advance in the hard disk 304 of the management apparatus 2.

Various modifications can be appropriately made in the embodiments of the invention in the scope of the technical idea shown in the claims.

What is claimed is:

1. A sample analyzing system, comprising:
a sample analyzer configured to analyze a sample; and
a management apparatus connected to the sample analyzer via a communication network,
wherein the management apparatus comprises:
a first memory that stores a computer program for the sample analyzer and manual data which corresponds to a version of the computer program and describes an operation procedure of the sample analyzer;
a first communication device configured to communicate with the sample analyzer; and
a first controller configured to transmit, via the first communication device to the sample analyzer, the computer program and the manual data corresponding to the version of the computer program which are stored in the first memory, and
the sample analyzer comprises:
a second communication device configured to communicate with the first communication device and to receive the computer program and the manual data transmitted from the first communication device;
a second memory configured to store several versions of the computer program and several versions of the manual data respectively corresponding to the several versions of the computer program received by the second communication device; and
a second controller configured to execute the computer program selected from the several versions of the computer program stored in the second memory.

2. The sample analyzing system according to claim 1, wherein a first version of the computer program is stored in the second memory of the sample analyzer, and
when transmitting a second version of the computer program which is a newer version than the first version of the computer program to the sample analyzer via the first communication device, the first controller of the management apparatus transmits manual data corresponding to the second version of the computer program to the sample analyzer via the first communication device.

3. The sample analyzing system according to claim 2, wherein the second controller of the sample analyzer transmits version information of the computer program which is stored in the second memory to the management apparatus via the second communication device, and
the first controller of the management apparatus determines whether or not the second version of the computer program which is a newer version than the first version of the computer program is stored in the first memory on the basis of the version information received via the first communication device from the sample analyzer, and when the second version of the computer program is stored in the first memory, the first controller transmits the second version of the computer program and manual data corresponding to the second version of the computer program to the sample analyzer via the first communication device.

4. The sample analyzing system according to claim 2, wherein when setting the second version of the computer program to be executable, the second controller of the sample analyzer preserves the first version of the computer program and manual data corresponding to the first version of the computer program which are stored in the second memory.

5. The sample analyzing system according to claim 4, wherein the second memory of the sample analyzer includes a first storage area in which the computer program which is transmitted from the management apparatus is stored, and a second storage area in which a computer program which is executed by the second controller is stored, and
the second controller sets the computer program to be executable by moving the computer program transmitted from the management apparatus to the second storage area from the first storage area of the second memory.

6. The sample analyzing system according to claim 1, wherein the second controller of the sample analyzer stores the computer program transmitted from the management apparatus in the second memory, and automatically sets the computer program stored in the second memory to be executable.

7. The sample analyzing system according to claim 6, wherein the second controller sets the computer program stored in the second memory to be executable when the sample analyzer is powered up.

8. The sample analyzing system according to claim 1, wherein the second controller of the sample analyzer backs up information stored in the sample analyzer before the computer program transmitted from the management apparatus is set to be executable.

9. The sample analyzing system according to claim 1, wherein the first controller of the management apparatus transmits the computer program and the manual data corresponding to the version of the computer program to the sample analyzer via the first communication device by a single transmission procedure.

10. The sample analyzing system according to claim 1, comprising
an automatic transmission setting section for setting whether or not the computer program and the manual data corresponding to the version of the computer program which are stored in the first memory of the management apparatus are automatically transmitted to the sample analyzer from the management apparatus.

11. The sample analyzing system according to claim 1, wherein the first memory of the management apparatus stores first manual data written in a first language and second manual data written in a second language as manual data corresponding to a version of a computer program,
the sample analyzer has language setting information for specifying a language of a manual for the sample analyzer, and
the first controller of the management apparatus transmits the first manual data or the second manual data to the sample analyzer via the first communication device on the basis of the language setting information of the sample analyzer.

12. The sample analyzing system according to claim 11, wherein the second controller of the sample analyzer transmits the language setting information to the management apparatus via the second communication device, and
the first controller of the management apparatus receives the language setting information which is transmitted from the sample analyzer via the first communication device.

13. The sample analyzing system according to claim 12, wherein the second controller of the sample analyzer transmits the language setting information to the management apparatus via the second communication device in association with version information of the computer program which is stored in the second memory.

14. A sample analyzer which is connected to a management apparatus via a communication network, comprising:
a receiving device configured to receive, from the management apparatus, a computer program and manual data which corresponds to a version of the computer program and describes an operation procedure of the sample analyzer;
a memory configured to store several versions of the computer program and several versions of the manual data respectively corresponding to the several versions of the computer program received by the receiving device; and
a controller configured to execute the computer program selected from the several versions of the computer program stored in the memory.

15. The sample analyzer according to claim 14, wherein the memory stores a first version of the computer program, and
when a second version of the computer program which is a newer version than the first version of the computer program stored in the memory is stored in the management apparatus, the controller receives the second version of the computer program and manual data corresponding to the second version of the computer program from the management apparatus via the receiving device.

16. The sample analyzer according to claim 15, wherein when setting the second version of the computer program to be executable, the controller preserves the first version of the computer program and manual data corresponding to the first version of the computer program which are stored in the memory.

17. The sample analyzer according to claim 14, wherein the controller stores the computer program transmitted from the management apparatus in the memory, and automatically sets the computer program stored in the memory to be executable.

18. The sample analyzer according to claim 17, wherein the controller sets the computer program stored in the memory to be executable when the sample analyzer is powered up.

* * * * *